United States Patent
Barnes et al.

(10) Patent No.: US 6,912,317 B1
(45) Date of Patent: Jun. 28, 2005

(54) MEDICAL IMAGE DATA COMPRESSION EMPLOYING IMAGE DESCRIPTIVE INFORMATION FOR OPTIMAL COMPRESSION

(75) Inventors: Robert D. Barnes, Palatine, IL (US); Robert C. Gemperline, Algonquin, IL (US)

(73) Assignee: General Electric Company, Schenectady, NY (US)

( * ) Notice: Subject to any disclaimer, the term of this patent is extended or adjusted under 35 U.S.C. 154(b) by 624 days.

(21) Appl. No.: 09/448,952

(22) Filed: Nov. 24, 1999

(51) Int. Cl.$^7$ ................................................ G06K 9/36
(52) U.S. Cl. ....................................... 382/239; 382/232
(58) Field of Search ................................ 382/128, 132, 382/166, 232, 235, 238, 239, 243; 375/240.02, 240.08, 240.12, 240.14; 341/51

(56) References Cited

U.S. PATENT DOCUMENTS

| | | | |
|---|---|---|---|
| 4,916,544 A | | 4/1990 | Lienard et al. .......... 358/262.1 |
| 5,289,548 A | | 2/1994 | Wilson et al. ................ 382/56 |
| 5,774,597 A | | 6/1998 | Wilson ........................ 382/250 |
| 5,779,634 A | * | 7/1998 | Ema et al. .................. 128/920 |
| 5,901,249 A | * | 5/1999 | Ito ............................... 382/128 |
| 5,938,607 A | * | 8/1999 | Jago et al. .................. 600/437 |
| 6,100,940 A | * | 8/2000 | Dieterich .................... 348/700 |
| 6,115,486 A | * | 9/2000 | Cantoni ...................... 382/128 |
| 6,198,837 B1 | * | 3/2001 | Sasano et al. .............. 382/132 |
| 6,310,981 B1 | * | 10/2001 | Makiyama et al. ......... 382/239 |
| 6,323,869 B1 | * | 11/2001 | Kohm et al. ................ 345/581 |
| 6,349,373 B2 | * | 2/2002 | Sitka et al. ..................... 705/2 |

* cited by examiner

Primary Examiner—Yon J. Couso
(74) Attorney, Agent, or Firm—Fletcher Yoder (57) ABSTRACT

An image data compression technique is disclosed in which image data compression is based at least partially upon information encoded in a descriptive portion of an image data file. The descriptive portion may be a header appended to image data. In medical diagnostic applications the descriptive data may include DICOM compliant data specifying imaging modality, anatomy or other features viewable in the reconstructed images, image matrix size, and so forth. Based upon the descriptive data, the image data files are analyzed and optimal compression algorithms are identified and selected. The image data files are then compressed in accordance with the selected algorithms. The algorithms may include appropriate compression code tables, desired lengths of subregions into which the image data stream is divided for compression, predictor algorithms used to determine relative entropy levels within the image data, and so forth.

28 Claims, 8 Drawing Sheets

16 – BIT LOSSLESS ENCODING
SCHEME 0 – MAX RATIO = 16:1

| HUFFMAN CODE PREFIX | CODE EXTENSION | DIFFERENCE d | CODE LENGTH | ENCODED RANGE WIDTH |
|---|---|---|---|---|
| 0 | | 0 | 1 | 0 |
| 100 | | +1 | 3 | +1 |
| 101 | | −1 | 3 | |
| 1100 | X | +2 TO +3 | 5 | +2 |
| 1101 | X | −2 TO −3 | 5 | |
| 11100 | XX | +4 TO +7 | 7 | +4 |
| 11101 | XX | −4 TO −7 | 7 | |
| 111100 | XXX | +8 TO +15 | 9 | +8 |
| 111101 | XXX | −8 TO −15 | 9 | |
| 1111100 | XXXX | +16 TO +31 | 11 | +16 |
| 1111101 | XXXX | −16 TO −31 | 11 | |
| 11111100 | XXXXX | +32 TO +63 | 13 | +32 |
| 11111101 | XXXXX | −32 TO −61 | 13 | |
| 111111100 | XXXXXX | +64 TO +127 | 15 | +64 |
| 111111101 | XXXXXX | −64 TO −127 | 15 | |
| 1111111100 | XXXXXXX | +128 TO +255 | 17 | +128 |
| 1111111101 | XXXXXXX | −128 TO −255 | 17 | |
| 11111111100 | XXXXXXXX | +256 TO +511 | 19 | +256 |
| 11111111101 | XXXXXXXX | −256 TO −511 | 19 | |
| 11111111110 <16 BITS) | | ACTUAL VALUE | 27 | |
| 11111111111 | | END OF BLOCK | 11 | |

FIG. 8

SCHEME 1 – MAX RATIO = 5.33:1

| HUFFMAN CODE PREFIX | CODE EXTENSION | DIFFERENCE d | CODE LENGTH | ENCODED RANGE WIDTH |
|---|---|---|---|---|
| 00 | X | 0 TO +1 | 3 | 1 |
| 01 | X | −1 TO −2 | 3 | |
| 100 | XX | +2 TO +5 | 5 | +4 |
| 101 | XX | −3 TO −6 | 5 | |
| 1100 | XXX | +6 TO +13 | 7 | +8 |
| 1101 | XXX | −7 TO −14 | 7 | |
| 11100 | XXXX | +14 TO +29 | 9 | +16 |
| 11101 | XXXX | −15 TO −30 | 9 | |
| 111100 | XXXXX | +30 TO +61 | 11 | +32 |
| 111101 | XXXXX | −31 TO −62 | 11 | |
| 1111100 | XXXXXX | +62 TO +125 | 13 | +64 |
| 1111101 | XXXXXX | −63 TO −126 | 13 | |
| 11111100 | XXXXXXX | +126 TO +253 | 15 | +128 |
| 11111101 | XXXXXXX | −127 TO −254 | 15 | |
| 111111100 | XXXXXXXX | +254 TO +509 | 17 | +256 |
| 111111101 | XXXXXXXX | −255 TO −510 | 17 | |
| 1111111100 | XXXXXXXXX | +510 TO +1021 | 19 | +512 |
| 1111111101 | XXXXXXXXX | −511 TO −1022 | 19 | |
| 1111111110 <16 BITS) | | ACTUAL VALUE | 26 | |
| 1111111111 | | END OF BLOCK | 10 | |

FIG. 9

SCHEME 2 — MAX RATIO = 4:1

| HUFFMAN CODE PREFIX | CODE EXTENSION | DIFFERENCE d | CODE LENGTH | ENCODED RANGE WIDTH |
|---|---|---|---|---|
| 00 | XX | 0 TO +3 | 4 | 3  ←—186 |
| 01 | XX | −1 TO −4 | 4 | |
| 100 | XXX | +4 TO +11 | 6 | +8 |
| 101 | XXX | −5 TO −12 | 6 | |
| 1100 | XXXX | +12 TO +27 | 8 | +16 |
| 1101 | XXXX | −13 TO −28 | 8 | |
| 11100 | XXXXX | +28 TO +59 | 10 | +32 |
| 11101 | XXXXX | −29 TO −60 | 10 | |
| 111100 | XXXXXX | +60 TO +123 | 12 | +64 |
| 111101 | XXXXXX | −61 TO −124 | 12 | |
| 1111100 | XXXXXXX | +124 TO +251 | 14 | +128 |
| 1111101 | XXXXXXX | −125 TO −252 | 14 | |
| 11111100 | XXXXXXXX | +252 TO +507 | 16 | +256 |
| 11111101 | XXXXXXXX | −253 TO −508 | 16 | |
| 111111100 | XXXXXXXXX | +508 TO +1019 | 18 | +512 |
| 111111101 | XXXXXXXXX | −509 TO −1020 | 18 | |
| 111111110 | <16 BITS) | ACTUAL VALUE | 25 | |
| 111111111 | | END OF BLOCK | 9 | |

FIG. 10

SCHEME 3 — MAX RATIO = 3.2:1

| HUFFMAN CODE PREFIX | CODE EXTENSION | DIFFERENCE d | CODE LENGTH | ENCODED RANGE WIDTH |
|---|---|---|---|---|
| 00 | XXX | 0 TO +7 | 5 | 7  ←—188 |
| 01 | XXX | −1 TO −8 | 5 | |
| 100 | XXXX | +8 TO +23 | 7 | +16 |
| 101 | XXXX | −9 TO −24 | 7 | |
| 1100 | XXXXX | +24 TO +55 | 9 | +32 |
| 1101 | XXXXX | −25 TO −56 | 9 | |
| 11100 | XXXXXX | +56 TO +119 | 11 | +64 |
| 11101 | XXXXXX | −57 TO −120 | 11 | |
| 111100 | XXXXXXX | +120 TO +247 | 13 | +128 |
| 111101 | XXXXXXX | −121 TO −248 | 13 | |
| 1111100 | XXXXXXXX | +248 TO +503 | 15 | +256 |
| 1111101 | XXXXXXXX | −249 TO −504 | 15 | |
| 11111100 | XXXXXXXXX | +504 TO +1015 | 17 | +512 |
| 11111101 | XXXXXXXXX | −505 TO −1016 | 17 | |
| 11111110 | <16 BITS) | ACTUAL VALUE | 24 | |
| 11111111 | | END OF BLOCK | 8 | |

FIG. 11

SCHEME 4 — MAX RATIO = 2.67:1

| HUFFMAN CODE PREFIX | CODE EXTENSION | DIFFERENCE d | CODE LENGTH | ENCODED RANGE WIDTH |
|---|---|---|---|---|
| 00 | XXXX | 0 TO +15 | 6 | 15 |
| 01 | XXXX | −1 TO −16 | 6 | |
| 100 | XXXXX | +16 TO +47 | 8 | +32 |
| 101 | XXXXX | −17 TO −48 | 8 | |
| 1100 | XXXXXX | +48 TO +111 | 10 | +64 |
| 1101 | XXXXXX | −49 TO −112 | 10 | |
| 11100 | XXXXXXX | +112 TO +239 | 12 | +128 |
| 11101 | XXXXXXX | −113 TO −240 | 12 | |
| 111100 | XXXXXXXX | +240 TO +495 | 14 | +256 |
| 111101 | XXXXXXXX | −241 TO −496 | 14 | |
| 1111100 | XXXXXXXXX | +496 TO +1007 | 16 | +512 |
| 1111101 | XXXXXXXXX | −497 TO −1008 | 16 | |
| 1111110 | <16 BITS) | ACTUAL VALUE | 23 | |
| 1111111 | | END OF BLOCK | 7 | |

SCHEME 5 — MAX RATIO = 2.29:1

| HUFFMAN CODE PREFIX | CODE EXTENSION | DIFFERENCE d | CODE LENGTH | ENCODED RANGE WIDTH |
|---|---|---|---|---|
| 00 | XXXXX | 0 TO +31 | 7 | 31 |
| 01 | XXXXX | −1 TO −32 | 7 | |
| 100 | XXXXXX | +32 TO +95 | 9 | +64 |
| 101 | XXXXXX | −33 TO −96 | 9 | |
| 1100 | XXXXXXX | +96 TO +223 | 11 | +128 |
| 1101 | XXXXXXX | −97 TO −224 | 11 | |
| 11100 | XXXXXXXX | +224 TO +479 | 13 | +256 |
| 11101 | XXXXXXXX | −225 TO −480 | 13 | |
| 111100 | XXXXXXXX | +480 TO +991 | 15 | +512 |
| 111101 | XXXXXXXX | −481 TO −992 | 15 | |
| 111110 | <16 BITS) | ACTUAL VALUE | 22 | |
| 111111 | | END OF BLOCK | 6 | |

MEDICAL IMAGE DATA COMPRESSION EMPLOYING IMAGE DESCRIPTIVE INFORMATION FOR OPTIMAL COMPRESSION

FIELD OF THE INVENTION

The present invention relates generally to a field of image compression and decompression, and more particularly to a technique for rapidly compressing and decompressing image data by optimal compression ratios based upon characteristics of the image itself, and utilizing information in the compressed image for decompression.

BACKGROUND OF THE INVENTION

Various techniques have been proposed and are currently in use for analyzing and compressing large data files, such as image data files. Image data files typically include streams of data descriptive of image characteristics, typically of intensities or other characteristics of individual pixel elements or pixels in a reconstructed image. In the medical field, for example, large image files are typically created during an image acquisition or encoding sequence, such as in an x-ray system, a magnetic resonance imaging system, a computed tomography imaging system, and so forth. The image data is then processed, such as to adjust dynamic ranges, enhance certain features shown in the image, and so forth, for storage, transmittal and display.

While image files may be stored in raw and processed formats, many image files are quite large, and would occupy considerable memory space. The increasing complexity of imaging systems also has led to the creation of very large image files, typically including more data as a result of the useful dynamic range of the imaging system and the size of the matrix of image pixels.

In addition to occupying large segments of available memory, large image files can be difficult or time consuming to transmit from one location to another. In a typical medical imaging application, for example, a scanner or other imaging device will typically create raw data which may be at least partially processed at the scanner. The data is then transmitted to other image processing circuitry, typically including a programmed computer, where the image data is further processed and enhanced. Ultimately, the image data is stored either locally at the system, or in a picture archiving and communications system (PACS) for later retrieval and analysis. In all of these data transmission steps, the large image data file must be accessed and transmitted from one device to another.

There is presently a need for improved image compression and decompression techniques which offer shorter compression and decompression times, while providing optimal compression of image data. There is a particular need for a lossless data compression technique which can be applied to a variety of image data types, particularly in the field of medical diagnostic imaging, for handling large data sets in an efficient manner from the points of view of computational requirements, memory requirements, and transmission bandwidth requirements.

SUMMARY OF THE INVENTION

The present invention provides an image data compression technique designed to respond to these needs. The technique offers extremely rapid compression and decompression of large image data files via a plurality of candidate compression algorithms. The compression algorithms are selected in a manner to provide optimal compression of subregions of the image data files. The selection of the compression algorithms is based at least partially upon data contained in a descriptive portion of the image data files.

In a medical diagnostic application, for example, the descriptive portion of the image data files may include data descriptive of an imaging modality, anatomy or other features viewable in the reconstructed images, image matrix size, and so forth. The data may be recognizable industry standard data, such as DICOM compliant data in the medical diagnostic imaging field.

The selection of the optimal compression algorithms may include selection of various algorithm parameters based upon prior knowledge of characteristics defined by the descriptive data. Thus, the algorithms may be selected from a family of compression code tables for translating image data into compressed data. Other parameters of the algorithms may include lengths of subregions into which the image data stream is divided for compression, and pixel value predictors used to determine characteristics of the image data, such as relative entropy levels.

BRIEF DESCRIPTION OF THE DRAWINGS

FIGS. 7, 8, 9, 10, 11 and 12 are reference lookup tables in the form of compression code tables used to optimally compress subregions of image data in accordance with the present technique during the process illustrated in FIG. 6.

DETAILED DESCRIPTION OF THE INVENTION

Figure 1:
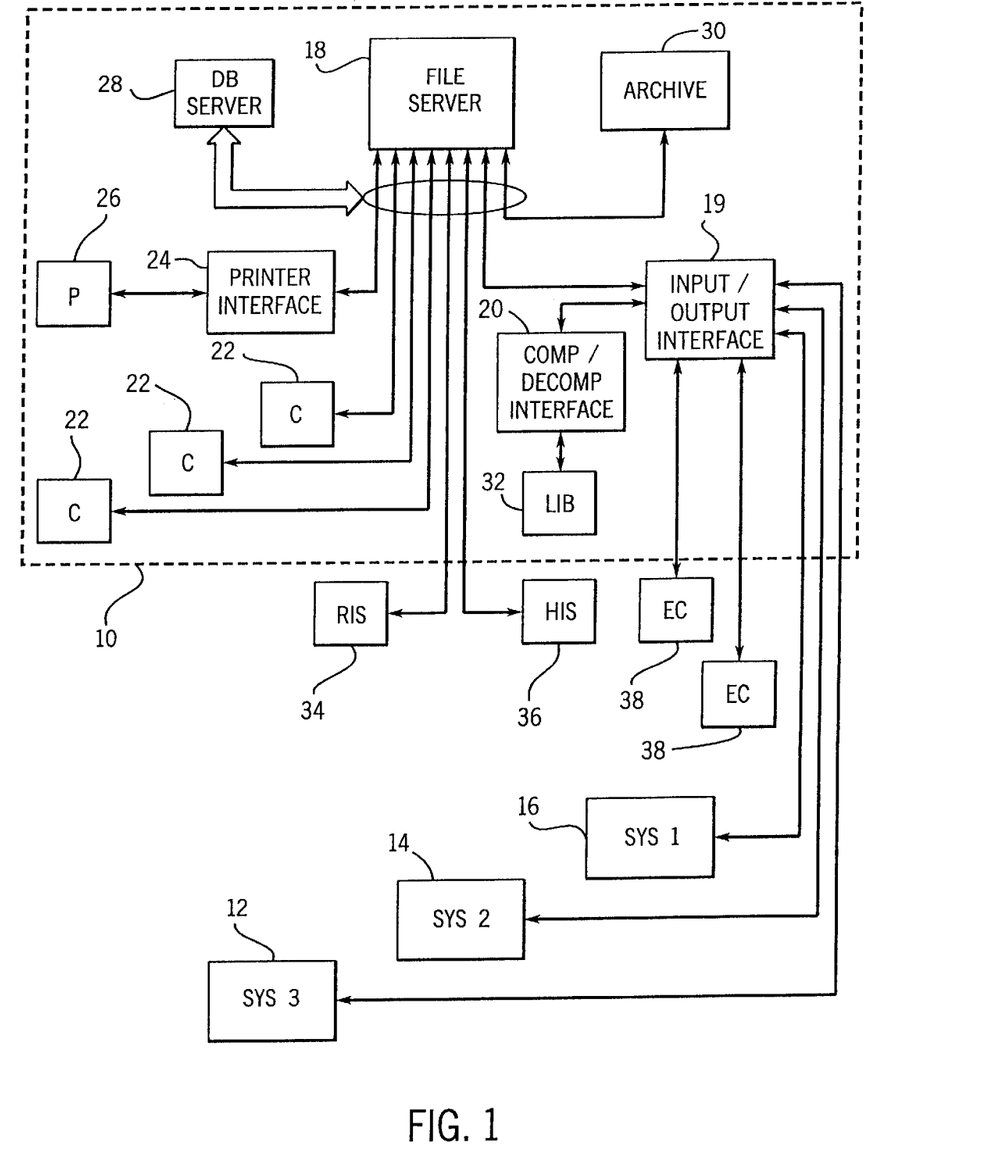
FIG. 1 is a diagrammatical representation of a picture archiving and communication system or PACS for receiving and storing image data in accordance with certain aspects of the present technique.

FIG. 1 illustrates a picture archive and communication system or PACS 10 for receiving, compressing and decompressing image data. In the illustrated embodiment, PACS 10 receives image data from several separate imaging systems designated by reference numerals 12, 14 and 16. As will be appreciated by those skilled in the art, the imaging systems may be of various type and modality, such as magnetic resonance imaging (MRI) systems, computed tomography (CT) systems, positron emission tomography (PET)

systems, radio fluoroscopy (RF), computed radiography (CR), ultrasound systems, and so forth. Moreover, the systems may include processing stations or digitizing stations, such as equipment designed to provide digitized image data based upon existing film or hard copy images. It should also be noted that the systems supplying the image data to the PACS may be located locally with respect to the PACS, such as in the same institution or facility, or may be entirely remote from the PACS, such as in an outlying clinic or affiliated institution. In the latter case, the image data may be transmitted via any suitable network link, including open networks, proprietary networks, virtual private networks, and so forth.

PACS 10 includes one or more file servers 18 designed to receive and process image data, and to make the image data available for decompression and review. Server 18 receives the image data through an input/output interface 19. Image data may be compressed in routines accessed through a compression/decompression interface 20. As described more fully below, interface 20 serves to compress the incoming image data rapidly and optimally, while maintaining descriptive image data available for reference by server 18 and other components of the PACS. Where desired, interface 20 may also serve to decompress image data accessed through the server. The server is also coupled to internal clients, as indicated at reference numeral 22, each client typically including a work station at which a radiologist, physician, or clinician may access image data from the server, decompress the image data, and view or output the image data as desired. Clients 22 may also input information, such as dictation of a radiologist following review of examination sequences. Similarly, server 18 may be coupled to one or more interfaces, such as a printer interface 24 designed to access and decompress image data, and to output hard copy images via a printer 26 or other peripheral.

Server 28 may associate image data, and other work flow information within the PACS by reference to one or more file servers 18. In the presently contemplated embodiment, database server 28 may include cross-referenced information regarding specific image sequences, referring or diagnosing physician information, patient information, background information, work list cross-references, and so forth. The information within database server 28 serves to facilitate storage and association of the image data files with one another, and to allow requesting clients to rapidly and accurately access image data files stored within the system. Similarly, server 18 is coupled to one or more archives 30, such as an optical storage system, which serve as repositories of large volumes of image data for backup and archiving purposes. Techniques for transferring image data between server 18, and any memory associated with server 18 forming a short term storage system, and archive 30, may follow any suitable data management scheme, such as to archive image data following review and dictation by a radiologist, or after a sufficient time has lapsed since the receipt or review of the image files.

In the illustrated embodiment, other components of the PACS system or institution may be integrated with the foregoing components to further enhance the system functionality. For example, as illustrated in FIG. 1, a compression/decompression library 32 is coupled to interface 20 and serves to store compression routines, algorithms, look up tables, and so forth, for access by interface 20 (or other system components) upon execution of compression and decompression routines (i.e. to store various routines, software versions, code tables, and so forth). In practice, interface 20 may be part of library 32. Library 32 may also be coupled to other components of the system, such as client stations 22 or printer interface 24, serving similarly as a library or store for the compression and decompression routines and algorithms. Although illustrated as a separate component in FIG. 1, it should be understood that library 32 may be included in any suitable server or memory device, including within server 18. Moreover, code defining the compression and decompression processes described below may be loaded directly into interface 20 and/or library 32, or may be loaded or updated via network links, including wide area networks, open networks, and so forth.

Additional systems may be linked to the PACS, such as directly to server 28, or through interfaces such as interface 19. In the embodiment illustrated in FIG. 1, a radiology department information system or RIS 34 is linked to server 18 to facilitate exchanges of data, typically cross-referencing data within database server 28, and a central or departmental information system or database. Similarly, a hospital information system or HIS 36 may be coupled to server 28 to similarly exchange database information, workflow information, and so forth. Where desired, such systems may be interfaced through data exchange software, or may be partially or fully integrated with the PACS system to provide access to data between the PACS database and radiology department or hospital databases, or to provide a single cross-referencing database. Similarly, external clients, as designated at reference numeral 38, may be interfaced with the PACS to enable images to be viewed at remote locations. Such external clients may employ decompression software, or may receive image files already decompressed by interface 20. Again, links to such external clients may be made through any suitable connection, such as wide area networks, virtual private networks, and so forth.

Figure 2:
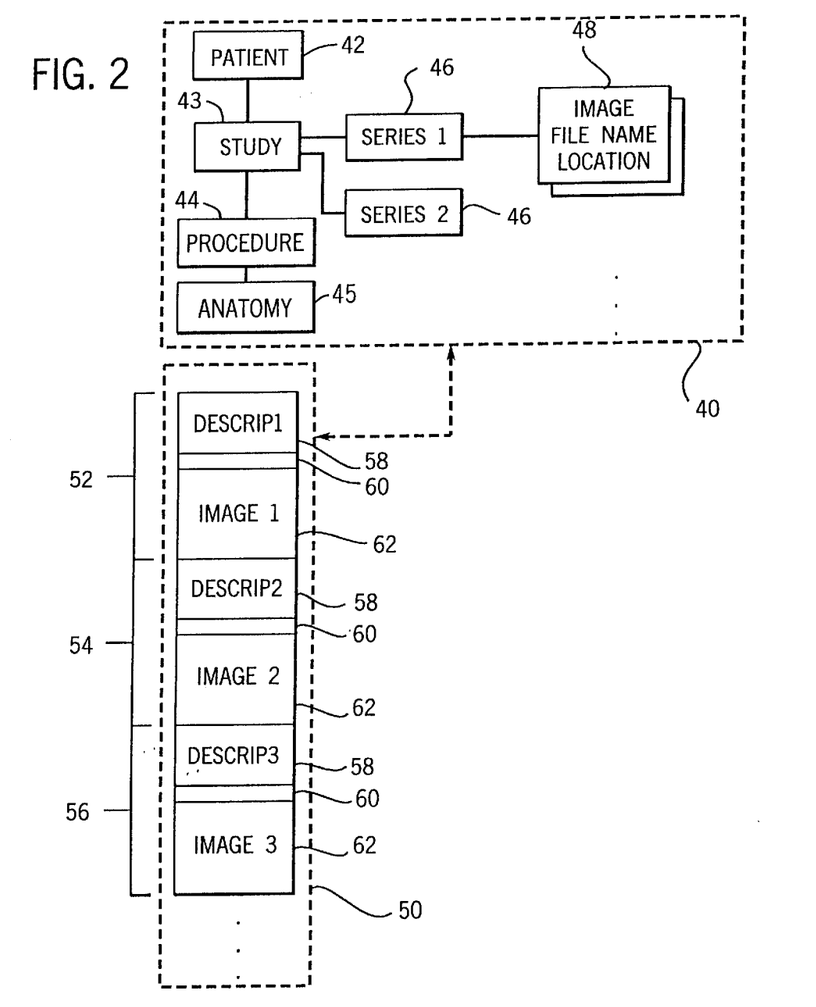
FIG. 2 is a diagrammatical representation of contents of a database for referencing stored image data in files containing multiple image data sets, compressed data, and descriptive information.

FIG. 2 illustrates in somewhat greater detail the type of cross-referencing data made available to clients 20, 22, 24, 30 through database server 28. The database entries, designated generally by reference numeral 40 in FIG. 2, will include cross-referenced information, including patient data 42, references to specific studies or examinations 43, references to specific procedures performed 44, references to anatomy imaged 45, and further references to specific image series 46 within the study or examination. As will be appreciated by those skilled in the art, such cross-referenced information may include further information regarding the time and date of the examination and series, the name of diagnosing, referring, and other physicians, the hospital or department where the images are created, and so forth. The database will also include address information identifying specific images, file names, and locations of the images as indicated at reference numeral 48. Where the PACS includes various associated memory devices or short term storage systems, these locations may be cross-referenced within the database and may be essentially hidden from the end user, the image files simply being accessed by the system for viewing from the specific storage location based upon cross-referenced information in the database.

As described more fully below, in accordance with certain aspects of the present technique, descriptive information is used to identify preferred or optimal compression routines used to compress image data. Such descriptive information is typically available from header sections of an image data string, also as described in detail below. However, information available from database server 28 may also serve as the basis for certain of the selections of the algorithms employed in the compression technique. Specifically database references may be relied upon for identifying such descriptive information as the procedures performed in an imaging sequence, specific anatomies or other features viewable in reconstructed images based upon the data, and so forth. Such information may also be available from the RIS 34 and from the HIS 36.

FIG. 2 also illustrates an exemplary image file cross-referenced by the database entries. As shown in FIG. 2, image file 50 includes a plurality of image data sets 52, 54 and 56. In a typical image file, a large number of such image sets may be defined by a continuous data stream. Each data set may be compressed in accordance with specific compression algorithms, including lossless compression algorithms as described below, lossy compression algorithms, wavelet algorithms, and the preferred compression code table-based optimal compression algorithm described below.

Within each image data set, a descriptive header 58 is provided, along with a compression header 60. The headers 58 and 60 are followed by compressed image data 62. The descriptive header 58 of each data set preferably includes industry-standard or recognizable descriptive information, such as DICOM compliant descriptive data. As will be appreciated by those skilled in the art, such descriptive information will typically include an identification of the patient, image, date of the study or series, modality of the system creating the image data, as well as additional information regarding specific anatomies or features visible in the reconstructed images. As described more fully below, such descriptive header data is preferably employed in the present technique for identification of optimal compression algorithms or routines used to compress the data within the compressed image data section 62. Data referring to the specific algorithm or routine used to compress the image data is then stored within compression header 60 for later reference in decompressing the image data. As described below, additional data is stored within the compressed image data, cross-referencing the algorithms identified in compression header 60 for use in decompressing the image data. Specifically, in a presently preferred embodiment, the compression header 60 includes identification of the length of subregions of the compressed image data, as well as references to specific optimal algorithms, in the form of compression code tables used to compress the subregions optimally.

Figure 3:
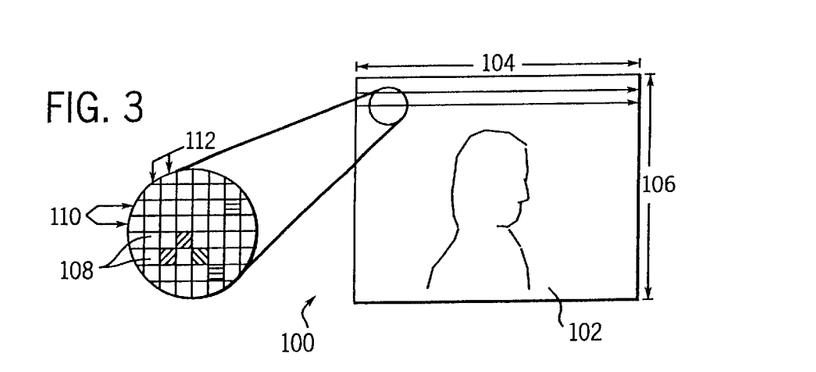
FIG. 3 is a representation of a typical image of the type received, compressed, and stored on the system of FIG. 1.

FIG. 3 illustrates a typical image which is encoded by packets of digitized data assembled in a continuous data stream which may be compressed and decompressed in the present techniques. The image, designated generally by the reference numeral 100, will typically include features of interest 102, such as specific anatomical features. In medical diagnostic applications, such features may include specific anatomies or regions of a patient viewable by virtue of the physics of the image acquisition modality, such as soft tissue in MRI system images, bone in x-ray images, and so forth. Each image is comprised of a matrix having a width 104 and a height 106 defined by the number and distribution of individual pixels 108. The pixels of the image matrix are arranged in rows 110 and columns 112, and will have varying characteristics which, when viewed in the reconstructed image, define the features of interest. In a typical medical diagnostic application, these characteristics will include gray level intensity or color. In the digitized data stream, each pixel is represented by binary code, with the binary code being appended to the descriptive header to aid in identification of the image and in its association with other images of a study. As noted above, such descriptive information may include industry standard information, such as DICOM compliant data.

Figure 4:
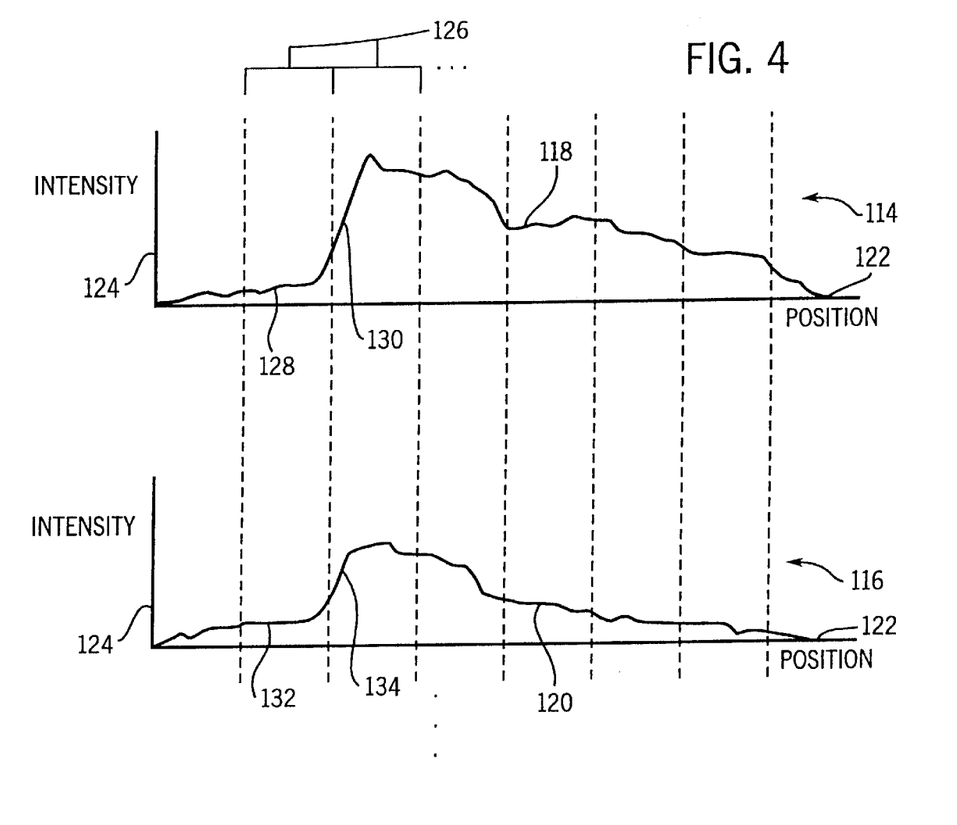
FIG. 4 is a graphical representation of intensities of pixelated data across an image, subdivided into subregions for compression of the subregions optimally based upon characteristics of the subregions.

FIG. 4 graphically represents intensities of pixel data defining an image across a pair of rows of the image matrix. Each row of the image matrix will include a series of pixels, each pixel being encoded by binary data descriptive of the pixel characteristics, typically intensity. Thus, lighter regions of the reconstructed image will correspond to pixels having a higher intensity level, with darker regions having a lower intensity level. When illustrated graphically, the intensity levels of the pixels across the image may form a contour or trace as shown in FIG. 4. Specifically, FIG. 4 illustrates a first row 114 lying adjacent to a second row 116, each row including a series of pixels having various intensities as indicated by traces 118 and 120, respectively. As will be appreciated by those skilled in the art, in practice, the graph of the pixel intensities would form a step-wise function along the position axis 122 and having amplitudes varying along the intensity axis 124.

It may be noted from FIG. 4 that in an actual image, variations in intensity along rows, and along columns as represented by correspondingly located intensities moving downwardly or upwardly through adjacent rows, will vary in accordance with the features represented in the reconstructed image. As illustrated in FIG. 4, row 114 includes areas of rising and declining intensity, including areas of both low intensity and high intensity. Row 116 includes areas of similar intensity, but varying by virtue of the features represented in the image. In accordance with the present technique, the image data stream is reduced to subregions as represented generally by reference numeral 126 in FIG. 4. While the subregions may be of different lengths (i.e. numbers of pixels), in the presently preferred embodiment, each subregion includes data encoding an equal number of pixels. Those skilled in the art will readily recognize, however, that after compression the actual length of codes for the subregion will vary depending upon the intensity of the pixels within the subregion and the dynamic range of the digital data encoding the pixel intensities. It should also be noted that where the row length of the image matrix is an integer multiple of the subregion width, individual subregions will align with one another moving down the image matrix as represented in FIG. 4. In general, however, the present technique is not limited to such integer multiple row widths.

Each subregion of the image data stream may be analyzed to identify entropy levels of the image data for compression purposes. In general, the entropy of the image data refers to the relative variation in the pixel intensities within each subregion. Thus, although a specific subregion may include pixels of a high intensity or a low intensity, where the intensity level is relatively stable or constant in the subregion, entropy is considered to be low. Such regions are shown in FIG. 4, for example, in portions of traces 114 and 116 indicated by reference numerals 128 and 132, respectively. On the contrary, where substantial variations in pixel intensity are encoded by the subregion data, the entropy level is considered high. Such regions are shown in FIG. 4 at reference numerals 130 and 134. It has been found that by subdividing the image data stream into subregions, which may have various lengths depending upon the image characteristics, and by analyzing the relative entropy level of each subregion, the subregions may be optimally compressed in accordance with one of several candidate compression algorithms. Specifically, the present technique employs a series of predefined compression code tables which serve to translate pixel prediction errors into compressed codes for each subregion. The specific compression code table selected for each subregion is a function of the entropy identified for the subregion in the compression routine.

Figure 5:
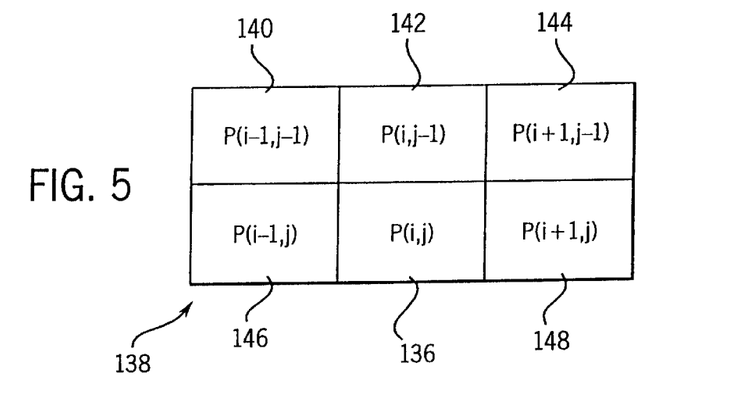
FIG. 5 is a diagrammatical representation of a pixel neighborhood used in the analysis of the image data for compression purposes.

As will be described more fully below, the present technique preferably employs pixel value predictors and identifies differences between predicted values of individual pixels (i.e. binary code for the pixel intensity or other characteristic) and the actual value for the respective pixels. In fact, several predictor algorithms may be employed, with the specific predictor being identified based upon image characteristics, such as characteristics encoded in a descriptive header for the image data stream. The predictors are based upon comparisons of target pixels, or pixels of interest, with neighboring pixels. FIG. 5 represents a pixel neighborhood which serves as the basis for references made in the predictor algorithms. The pixel neighborhood, identified by reference numeral 138 in FIG. 5, includes the pixel of interest 136, designated p(i, j). Neighboring pixels include a "northwest" pixel 140, designated p(i−1, j−1), a "north" pixel 142 designated p(i, j−1), a "northeast" pixel 144 designated p(i+1, j−1), a "west" pixel 146 designated p(i−1, j). Some or all of these pixels may be employed in the predictor algorithm, or other additional pixels may be provided in a larger neighborhood.

Figure 6:
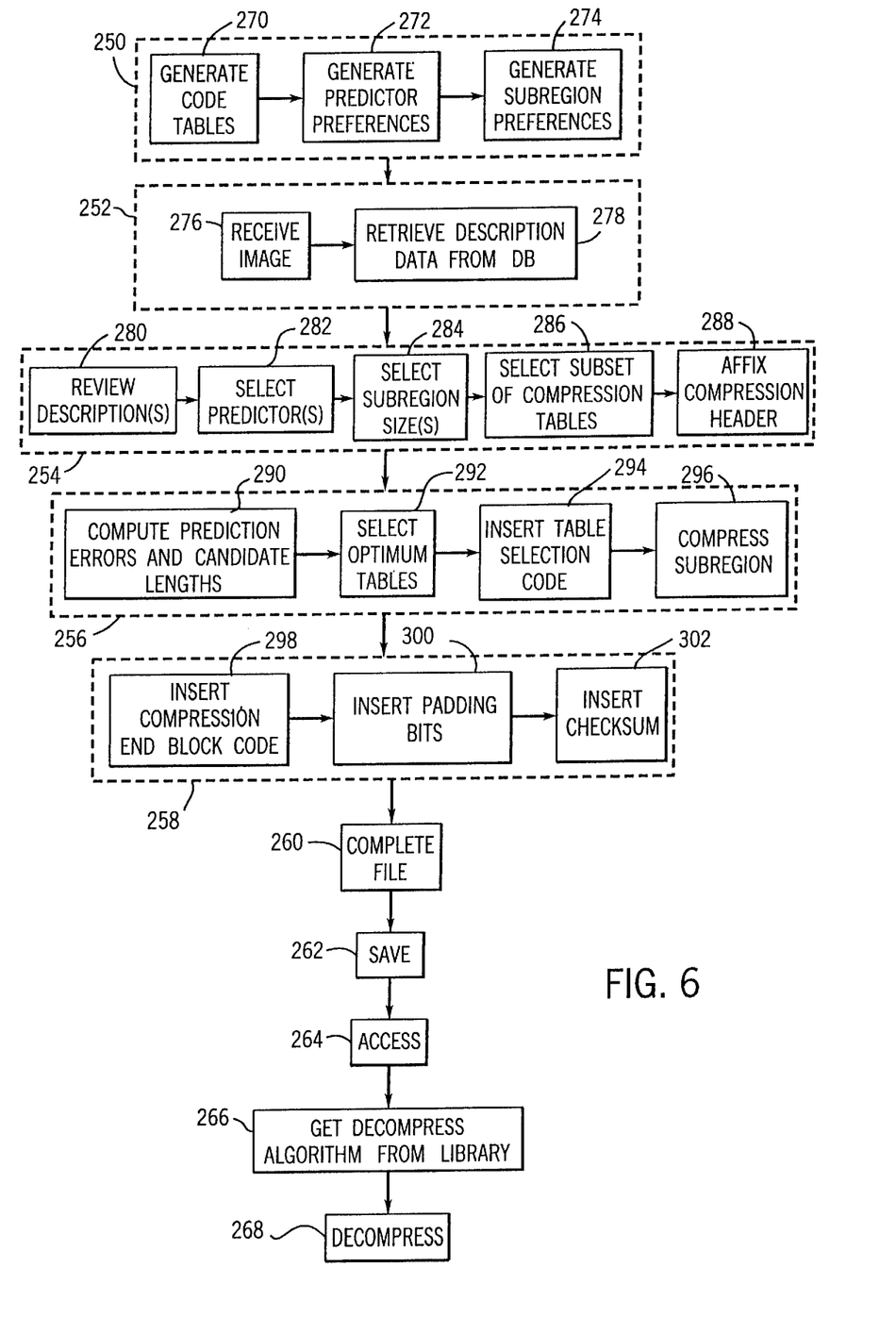
FIG. 6 is a flow chart illustrating exemplary control logic for compressing and decompressing image data in accordance with aspects of the present technique.
Figure 9:
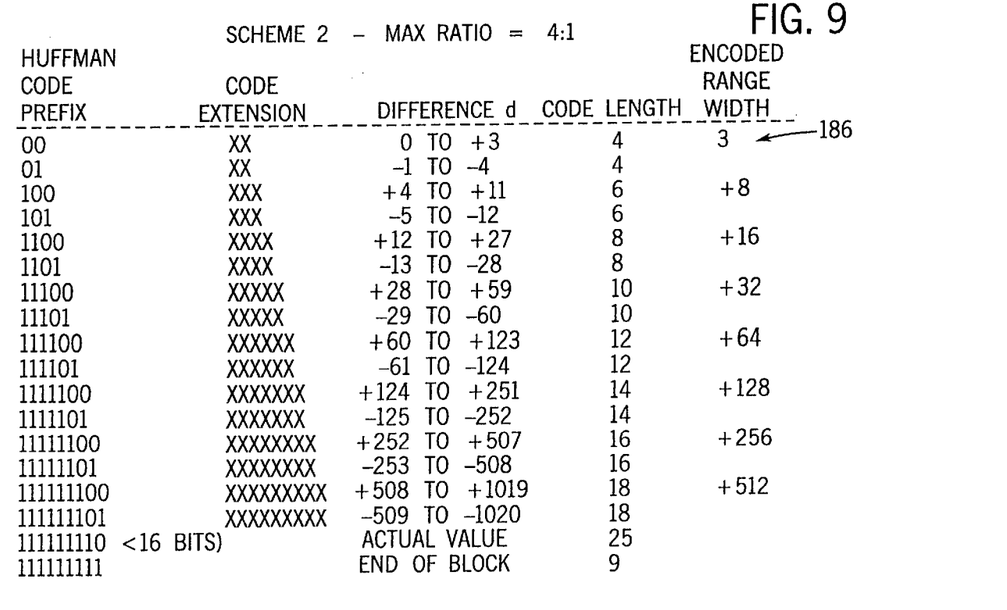
Figure 10:
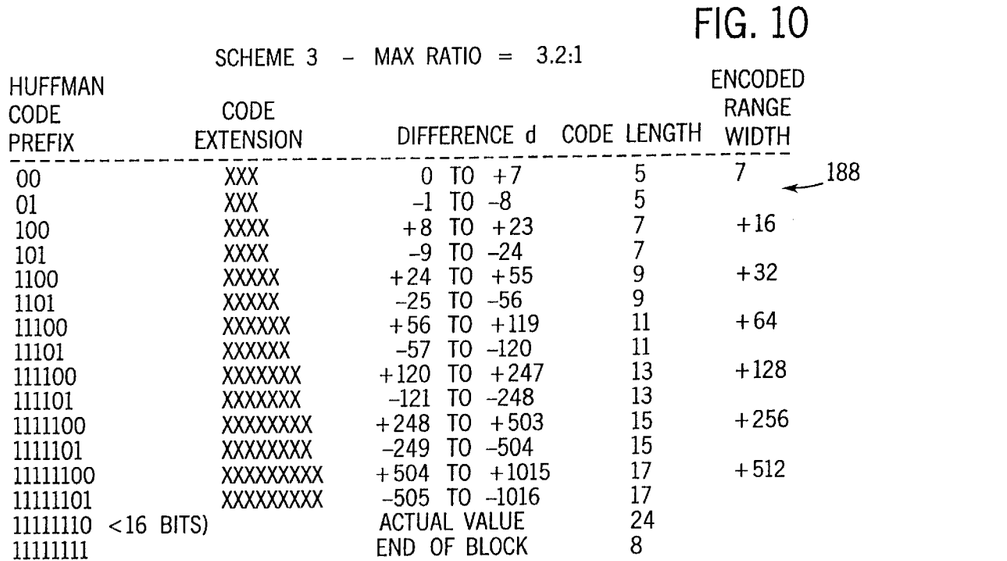
Figure 11:
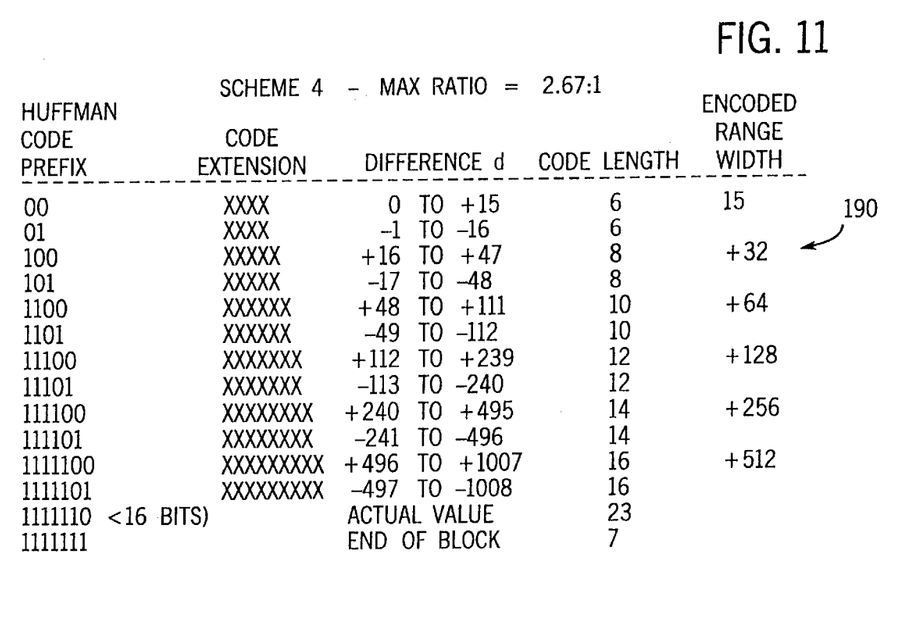

The preferred technique for compressing the image data stream in the system described above to create hybrid compressed image data files is summarized in FIG. 6. The control logic may be subdivided into a series of logical blocks or segments, including a configuration segment 250 in which optimal compression algorithms, tables, predictor preferences, block or subregion length preferences, and so forth, are established. In a data access and retrieval segment 252 the image data to be compressed is received, as is descriptive information from database server 28, if used. In an evaluation segment 254 the images are evaluated based upon the algorithms and preferences established in configuration segment 250. In a compression segment 256 certain values are computed and selected for the compression routine, and the image data is compressed to create the resulting compressed file. File code is added to the compressed data in a final segment 258. The file is then completed at step 260 and stored at step 262. The compression and decompression logic is then completed by eventual access of the compressed image file at step 264, retrieval of a decompression algorithm or algorithms at step 266 and decompression at step 268 for viewing and output. The foregoing logical segments and processes will be described below in greater detail.

The configuration segment 250 of the control logic includes steps of configuring the specific compression, predictor and block or subregion algorithms employed in the routine. Thus, at step 270 a series of compression code tables are generated for optimally compressing subregions of image data based upon relative entropy levels as indicated by prediction errors. As will be appreciated by those skilled in the art, such compression code tables serve to cross-reference original values with compressed values, generally in accordance with anticipated distributions or frequencies of occurrence of the original values. In the presently preferred embodiment, a series of compression code tables are established based upon analysis of typical images to be compressed by the routine. While the specific coding and ranges implemented in the compression code tables vary, and will generally be determined in specific applications empirically, examples of several such compression code tables are illustrated in FIGS. 7–12.

Referring to FIGS. 7–12, each compression code table, such as table 170 in FIG. 7, comprises a series of compressed data values 172 cross-referenced to original image parameters 174. In the example illustrated in the Figures, analysis may include an indication of the resulting code links in bits, as indicated by reference numeral 176, and the span of code translated by each table entry, as indicated by reference numeral 178. In the illustrated embodiment, the compressed data code of column 172 translates difference values of column 174 as identified by application of predictors in the compression routine, followed by determination of the differences between the predicted and actual values. Thus, by way of example, where a difference value of 1 is identified based upon a predictor algorithm as described below, table 170 provides a compressed data code of 100. Again, it should be noted that the difference value does not generally represent the value of the encoded pixel itself, but a difference between a predicted value and an actual value. Thus, in a code length of 3 bits, summarized in column 176 of table 170, the pixel of interest differing from the predicted value by 1 will obtain a compressed data value of 100, although the pixel value itself may be considerably longer. As also may be seen in FIG. 7, the compressed data codes provided in column 172 may be summarized as including a first portion 180 designating the level within the table, followed by a second portion 182 which indicates the position within the level or range. Thus, for example, in the case of the table of FIG. 7, a difference range of from −2 to −3 would be encoded as 1101 followed by an additional bit set to a value of 0 or 1 depending upon whether the difference is −2 or −3. At an upper limit of the range, the compressed data code is taken to be the actual value of the individual pixel as described below with reference to FIG. 13.

As can be seen from the Figures, the compression code tables for translating prediction errors or differences to compressed code are established to provide a range of coding appropriate to the levels or variations in the difference values for each subregion of the data stream. Specifically, table 170 of FIG. 7 is adapted to a lowest entropy level as indicated by the low difference variation (zero) accommodated by the shortest code in the table and the relatively fine steps between the difference levels. FIG. 8 represents a second compression code table 184 providing for relatively higher entropy as indicated by the relatively broader maximum levels accommodated by the table and the relatively higher difference ranges as compared to table 170 of FIG. 7. FIGS. 9, 10, 11 and 12 provide additional examples of compression code tables 186, 188, 190 and 192, respectively, for encoding successively higher entropy levels as indicated by prediction errors or differences within the various subregions. In the present embodiment illustrated, the code tables are constructed using a Huffman code-based prefix and a multibit extension.

Figure 12:
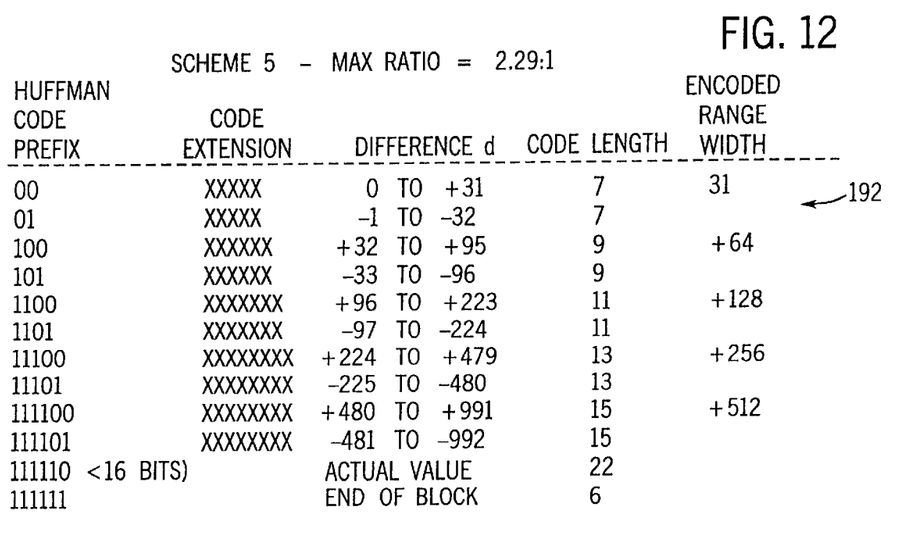

It should be noted that the compression ratio provided by each of the compression code tables in the family of tables varies depending upon the relative entropy level to be accommodated. Thus, table 170 of FIG. 7 provides a relatively high maximum compression ratio of 16:1, while table 192 of FIG. 12 provides a lower maximum compression ratio of 2.29:1. However, it has been found that the use of a plurality of different compression code tables to accommodate the different entropies of the data stream subregions results in excellent compression due to the use of compressed data code lengths optimally selected to accommodate the variations in prediction differences for the subregions.

It has been found that for specific types of images or for images having specific typical characteristics, various entropy levels may be anticipated. For example, in medical diagnostic imaging, relatively high entropy levels may be expected for specific modalities, such as CT and MRI data. Other imaging modalities may provide images with relatively lower variations in the image intensity levels, reflected by lower entropy values and correspondingly lower prediction differences. Moreover, it has been found that specific image types may provide higher or lower characteristic entropy values. In the medical diagnostics field, such image types may include specific anatomies, such as chest, head, extremities, and so forth, providing more or less variation, and stronger or weaker edge lines and contrast. The specific family of compression code tables, then, are preferably established based upon the typical images to be compressed by the system.

Returning to FIG. 6, with the family of compression code tables generated and stored at step 270, configuration segment 250 continues with generation of predictor preferences at indicated at step 272. As described above, rather than employ actual pixel intensity values for encoding in the present compression technique, difference values may be employed based upon the predictor algorithms. The predictor algorithms generally produce relatively low values in low entropy regions of the image, and relatively higher values in higher entropy regions. However, the use of prediction errors for the data compression will generally result in compression of values which are lower (i.e. shorter in length) than the original data stream code values due to the relatively gradual progression of intensity variations over the image.

In the presently preferred embodiment, one or more of several predictor algorithms may be employed. Referring again to FIG. 5, in a simple and straightforward algorithm, the value of each pixel $p(i, j)$ is predicted to be the value of the immediately preceding pixel $p(i-1, j)$. This predictor algorithm provides a computationally extremely efficient tool for the prediction of each pixel value, with the first pixel in the image being estimated at a value of zero. The difference value is then generated by finding the absolute value of the difference between the predicted value and the actual value for the pixel of interest. The resulting difference values form a matrix of equal size to the original image matrix.

Several alternative predictor algorithms are presently contemplated, and others may be employed as well. In the presently preferred embodiment, these predictor algorithms may be summarized as follows:

$$Ip(i, j)=Ip(i-1, j) \quad (P1);$$

$$Ip(i, j)=Ip(i-1, j)+Ip(i, j-1)-Ip(i-1, j-1) \quad (P2);$$

$$Ip(i, j)=((3*(Ip(i-1, j))+Ip(i-1, j-1)+Ip(i, j-1)+Ip(i+1, j-1))/6 (P3);$$

$$Ip(i, j)=((-2*I(i-1, j-1))+(3*Ip(i, j-1))+(3*Ip(i-1, j)))/4 \quad (P4);$$

$$Ip(i, j)=((-5*I(i-1, j-1))+(7*Ip(i, j-1))+Ip(i+1, j-1)+(9*Ip(i-1, j)))/12 \quad (P5);$$

$$Ip(i, j)=Ip(i, j-1)+Ip(i-1, j))/2 \quad (P6);$$

where the notation "I" represents the pixel intensity, and the individual pixel designations are mapped in accordance with FIG. 5.

Again, it has been found that various predictors are particularly useful for various types of images, images resulting from various modalities, and various features or anatomies visible in the reconstructed image. For example, the predictor algorithm P1 provides an extremely simple and rapid "last value" estimate of each current pixel value. Predictor P2 provides some degree of edge detection capability, but may accentuate the influence of noise in the image. The third predictor value P3 is a linear predictor shown useful on certain image types and employs values for more of the surrounding pixels, weighting the last value more heavily. In practice, the predictor preferences generated at step 272 of FIG. 6 will follow empirical results for various image types and modalities.

The final step illustrated in segment 250 of the control logic of FIG. 6 is the generation of subregion preferences for the division of the image data stream into subregions. As indicated above, while the lengths of subregions of the image data stream may be different or may vary depending upon such factors as the entropy level, in the presently preferred configuration, the subregion lengths are set equal to one another, but may vary depending upon such factors as the modality originating the image data, the image type, anatomy illustrated in the reconstructed image, and so forth. For example, subregion lengths of 32 pixels are presently set to a default, but alternative subregion lengths of 8, 16, 24, or more than 32 pixels, are contemplated. In general, the preferences set at step 274 in the present embodiment are dependent upon the number of columns in the image matrix, with subregion lengths of 8 being used for matrices having 64 columns or less, subregion lengths of 16 being used for matrices having 128 columns or less, and so forth. To reduce the computational complexity and to improve speed, in the presently preferred embodiment, the subregions are taken along the major direction or axis (i.e. rows or columns) of the image matrix, depending upon the direction in which the data is stored. Also, the subregions are preferably one dimensional only.

With the compression algorithms, tables, predictor preferences, and subregion size preferences set, the control logic illustrated in FIG. 6 advances through segment 252. In that segment of the logic, the image data is received as indicated at step 276. As noted above, the image data may be directly received from an external source, or may be accessed from a memory within the PACS itself. At step 278, any descriptive information used to select algorithms or parameters of the compression routine are retrieved from the database server. As noted above, such descriptive information may be stored in databases, and may complement the information contained within the descriptive header of the image data stream.

Following segment 252, control advances to evaluation segment 254. Within this segment, the image data is reviewed for descriptive information as indicated step 280. As described above, where descriptive information is available, such as DICOM compliant data in a descriptive header section of the image data stream or descriptive data from the database, some or all of this data is reviewed at step 280. Based upon the preferences set in the configuration segment 272, predictors are selected at step 282 depending upon the image characteristics identified as step 280. Again, these may include the modality of the originating imaging system, the study type or anatomy featured in the image, the number of columns in the image, the number of rows, and so forth. Moreover, other factors may be considered in selecting the predictors at step 282, such as the computational efficiency desired, the processing power of the system, and so forth, with computationally efficient predictors being selected where such processor capabilities are limited, or where additional speed is desired. At step 284, the subregion size for division of the image data stream into subregions is selected in accordance with the preferences established at step 274. Again, step 284 may consist of a default selection, which may be altered depending upon some or all of the characteristics or factors considered for selection of the predictors.

Evaluation segment 254 continues with the selection of a subset of compression tables, where appropriate, as indicated at step 286. In particular, based upon certain image characteristics, it may be useful to preselect certain compression tables as defaults. For example, specific image types originating in specific modalities, such as CT or MR images, may be best compressed with specific candidate tables which may be selected at step 286. At step 288 a compression header is affixed to the image data. As described below, this compression header will contain code identifying the version of the compression routine, the predictors selected at step 282, the subregion sizes selected at step 284, and so forth.

At compression segment 256 of the control logic, a set of prediction errors or difference values are computed at step 290. As noted above, these values are based upon application of one or more of the predictor algorithms selected at step 282, and by subsequently comparing the predicted values with the actual values for each pixel to determine the prediction error or difference. The resulting prediction errors then form a data stream with the first pixel being assigned its actual value, followed by the difference values for each pixel of the subregion.

The present technique provides for optimal compression of each of the subregions based upon appropriate selection of tables from the family of compression code tables established at step 270. To determine which tables provide best compression, at step 290 of the control logic of FIG. 6, candidate lengths of compressed data are computed by application of each of the candidate compression code tables to the data resulting from application of the predictor algorithms. The total data stream length for each subregion is summed for each case (i.e. application of each of the compression code tables). Following completion of each subregion, the resulting sums are compared to identify which compression code table results in the shortest data stream for the subregion. The corresponding compression code table is then selected as indicated at step 292. At step 294, code identifying the selected table for each subregion is then inserted into the compressed data and its header, as described in greater detail below.

As noted above, evaluation segment 254 or compression segment 256 may include defaults and constraints on the selection of the optimal code tables. For example, depending upon such factors as the bit depth of the image data to be encoded, certain default selections among the compression code tables may be made, such as selection of the first four tables for bit depths of 8 or less. In addition, certain preferences for designated compression code tables may be made in this selection process, depending upon such factors as the modality originating the image data. By way of example, CT and MRI data may tend to encode higher transitions of pixel intensities, corresponding to higher entropy regions. Accordingly, preferences may be included in the selection of the compression code tables, depending upon the descriptive data reviewed at step 280, such as to prefer one or more higher entropy tables for images originating in such modalities. Finally, in the presently preferred embodiment, code will be inserted directly into the compressed data stream to provide an indication of which of the selected tables is employed for compressing the individual subregions. To optimize the compression, it may be desirable to limit the number of tables which may be selected in the preprocess segment of the control logic to a number which may be conveniently coded in a limited number of bits, such as 2 bits of data. Thus, where table identification codes are to be provided in 2 bits, a constraint may be imposed in the preprocess segment such that only four of the candidate tables may be selected for the compression. Where an additional bit is available for identification of the tables, 8 candidate tables may be selected and encoded.

At step 294 key code for the subregion compression is inserted into the compressed data stream, immediately preceding the compressed subregion data. As noted above, where four candidate tables are employed for the compression, the code inserted at step 294 may include a pair of designated bits. The compression header created at step 288 cross references this key code to the selected compression tables. At step 296, the image data for the subregion is compressed by application of the selected compression code table. The series of steps of segment 256 is repeated for each subregion of the image until the entire image is compressed.

In final segment 258 the compressed data for each image is completed. Specifically, at step 298, a compression end block is added to the compressed data. At step 300, padding bits are inserted following the compression end block. Finally, at step 302 a checksum value computed through the compression process is added to the compressed data to provide a means for verifying proper decompression. The position and type of code added to the compressed data during segment 258 is described more fully below with reference to FIG. 13.

Where a descriptive header is provided for the original image data, the descriptive header is preferably replaced adjacent to the compression header to complete the image file as indicated at step 260. It will be noted that the resulting data file is a hybrid compressed data file in which the descriptive header data is readable for image management, access, transmission, and similar purposes, while the bulk of the image data is optimally compressed as described above. At step 262, the resulting file is saved, typically in a short term storage system, or in an archive. At step 264 the image is accessed for reviewing, analysis, hard copy creation, and so forth. Upon access of the image, the decompression algorithms identified in the hybrid compressed data file are retrieved for decompression, and the compressed image data is decompressed, as indicated at step 266. This decompression follows the compression header information, with the same compression code tables being employed to decompress the data as were employed to compress it for each subregion. This application of the compression code tables results in identification of the prediction errors or differences on which the compression was based, and the specific predictor algorithm or algorithms employed to generate the differences are then used to regenerate the original image data in a lossless fashion.

Figure 13:
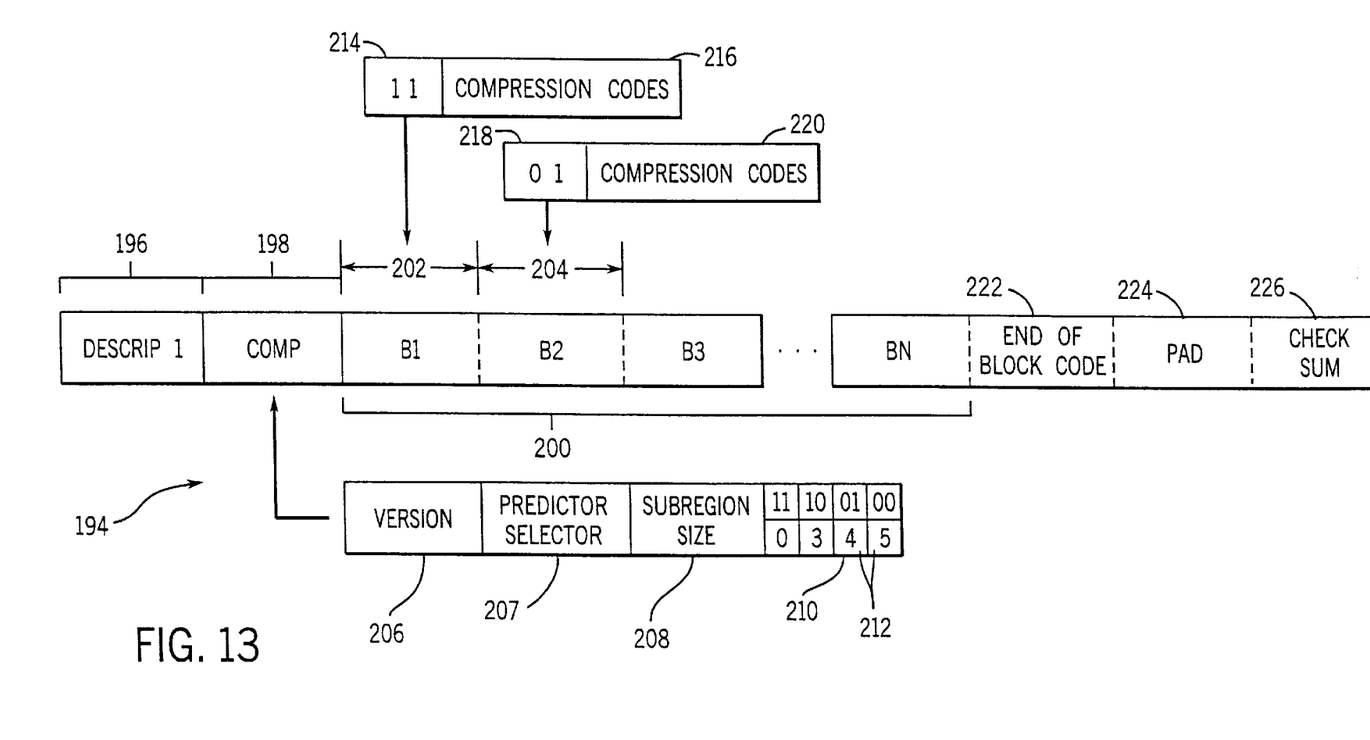
FIG. 13 is a diagrammatical representation of an exemplary image data set, including a descriptive header, a compression header, and blocks of compressed data by subregion.

FIG. 13 represents an image data set compressed in accordance with the foregoing technique. The image data set, designated generally by the reference numeral 194, includes the descriptive header 196 appended at step 160, along with the compression header 198 affixed at step 192. Following the compression header 198 is the compressed image data 200 which includes compressed image subregions 202, 204 and so forth. Each compressed data subregion, in turn, includes an identification of the algorithm or algorithms (e.g. compression code tables) used to encode the subregion, followed by the actual compressed data.

FIG. 13 also illustrates a presently contemplated format for a compression header 198. As shown in FIG. 13, the compression header includes an identification of the compression routine version 206, followed by an identification of the predictors used in the compression process 207, and identification of the subregion length at reference numeral 208. A compression algorithm identification segment 210 is then inserted in the compression header to identify which of the compression algorithms (e.g. compression code tables) were selected for the compression, and the manner in which each table is encoded in the data stream for each subregion. In the example of FIG. 13, for example, tables 0, 3, 4 and 5 were selected, as indicated at reference numeral 212, with each table being identified by a 2 bit binary code to be found within the first 2 bits of the compressed data for each subregion.

FIG. 13 also illustrates the format in the presently preferred embodiment for the compressed data code for each image subregion 202, 204, and so forth. In the illustrated embodiment, a first portion of each subregion includes an identification of the compression table used to compress the subregion data, as indicated at reference numeral 214 for subregion 202, and reference numeral 218 for subregion 204. This key code is followed by the compression codes as indicated at reference numerals 216 and 220, respectively. Finally, FIG. 13 illustrates the code inserted at the end of each compressed image file, or portion of a file. Specifically, following the last subregion BN of the image, the end of block code portion 222 is affixed. As noted above, this end of block code signals the end of an image, or may be used to signal the end of a portion of an image, where the data compression routine is changed within a single image, such as due to large variations in the image data entropy. The padding code is inserted as indicated at reference numeral 224. This code may be of variable size as needed to complete the compressed data file on a whole word length. Finally, a 32 bit checksum portion 226 is added to complete the compressed data.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. For example, the foregoing technique may be used on both images composed of varying gray levels, as well as on color images. As will be appreciated by those skilled in the art, color images will typically consist of various color components, which produce the appearance of color variations due to their respective intensities. The foregoing technique may be used either with or without separating the color components from one another, but is preferably applied by separating the color components and processing (i.e. compressing) the components in groups. Similarly, multiframe images may be accommodated in the present technique. As will be appreciated by those skilled in the art, such images typically comprise a number of separate images encoded by rows and columns, without separate descriptive headers (e.g. DICOM compliant headers) positioned between the separate images. In such cases, code identifying offsets in the compressed data corresponding to locations of different image frames is preferably inserted into the descriptive header of the hybrid compressed data file.

What is claimed is:

1. A method for generating a hybrid compressed/uncompressed image file, the method comprising the steps of:
   (a) accessing descriptive data for an image data file from a descriptive database;
   (b) accessing the image data file including a descriptive header and appended image data;
   (c) analyzing the descriptive header to identify characteristics of the image data;
   (d) selecting a data compression routine from a plurality of candidate routines based upon the characteristics, wherein the characteristics include a medical imaging modality; and
   (e) forming a hybrid compressed/uncompressed image file by compressing the image data in accordance with the selected routine, and appending the compressed image data sting to the uncompressed header.

2. The method of claim 1, wherein the descriptive header includes DICOM compliant descriptive data.

3. The method of claim 1, wherein the descriptive database is a PACS database.

4. The method of claim 1, wherein the characteristics include anatomy viewable in a reconstructed image.

5. The method of claim 1, including the further step of accessing the compression routine from a compression library.

6. The method of claim 1, wherein the compression routine includes analysis of the image data by subregions and selection of an optimal compression algorithm for each subregion.

7. The method of claim 6, wherein lengths of the subregions are selected based upon the characteristics identified in step (c).

8. The method of claim 6, wherein the optimal compression algorithms are selected based upon error predication analysis performed on the image data within each subregion.

9. The method of claim 8, wherein the characteristics include a description of anatomical features visible in a reconstructed image based upon the image file.

10. The method of claim 1, wherein the image data file is one of a plurality of image data files in a continuous data set, and wherein each image data file of the continuous data set is compressed in accordance with a respective descriptive header.

11. The method of claim 1, wherein the compression routines include a plurality of image data entropy predictive algorithms.

12. The method of claim 1, wherein the characteristics include bit depth of the image data.

13. The method of claim 1, wherein the characteristics include a procedure employed for creation of the image data.

14. The method of claim 1, wherein the characteristics include a number of columns of an image matrix represented by the image data.

15. A method for compressing medical diagnostic images, the method comprising the steps of:
   (a) acquiring image data representative of an anatomical feature of interest;
   (b) creating an image data file by attaching a descriptive header to the image data;
   (c) analyzing the descriptive header to identify characteristics of interest in the image data file, wherein the descriptive header includes an identification of a modality of the medical imaging system;
   (d) selecting an image data compression routine based at least partially on the characteristics, wherein the compression routine is selected at least partially based upon the modality; and
   (e) compressing at least the image data in accordance with the selected compression routine.

16. The method of claim 15, wherein the descriptive header includes DICOM compliant descriptive data and is attached to the image data at a medical imaging system.

17. The method of claim 15, wherein the steps of selecting the compression routine and compressing the image data are performed by a picture archiving and communication system, and wherein a compressed image file including the compressed image data is stored on a server of the system.

18. The method of claim 15, wherein the descriptive header is not compressed.

19. The method of claim 15, including the further step of accessing the compression routine from a compression library.

20. The method of claim 15, wherein the compression routine includes analysis of the image data by subregions and selection of an optimal compression algorithm for each subregion.

21. The method of claim 20, wherein lengths of the subregions are selected based upon the characteristics identified in step (c).

22. The method of claim 20, wherein the optimal compression algorithms are selected based upon error predication analysis performed on the image data within each subregion.

23. The method of claim 20, wherein the characteristics include a description of anatomical features visible in a reconstructed image based upon the image file.

24. The method of claim 15, wherein the image data file is one of a plurality of image data files in a continuous data set, and wherein each image data of each image data file of the continuous data set is compressed in accordance with a respective descriptive header.

25. The method of claim 15, wherein the compression routine includes a plurality of image data entropy predictive algorithms.

26. A computer program for compressing image data, the computer program comprising:

a machine readable medium for supporting machine readable code; and configuration code stored on the machine readable medium for analyzing a portion of an image data file for descriptive image characteristics, selecting a compression algorithm from a plurality of candidate algorithms based upon the descriptive image characteristics, wherein the descriptive image characteristics include a medical imaging modality, and compressing at least a portion of the image data file based in accordance with the selected compression algorithm.

27. The computer program of claim 26, comprising a second machine readable medium, and wherein the code includes the plurality of candidate algorithms stored in a library on the second machine readable medium.

28. The computer program of claim 26, wherein the descriptive image characteristics are coded in a header portion of the image data file, and wherein the configuration code does not compress the header portion.

* * * * *